(12) United States Patent
Bernabei

(10) Patent No.: US 7,052,503 B2
(45) Date of Patent: May 30, 2006

(54) DERMABRASION APPARATUS AND METHOD HAVING OVAL-SHAPED MIXING BOTTLE

(75) Inventor: Gian Franco Bernabei, Florence (IT)

(73) Assignee: Mattioli Engineering, Ltd., London (GB)

(*) Notice: Subject to any disclaimer, the term of this patent is extended or adjusted under 35 U.S.C. 154(b) by 423 days.

(21) Appl. No.: 10/115,970

(22) Filed: Apr. 5, 2002

(65) Prior Publication Data
US 2002/0107529 A1 Aug. 8, 2002

Related U.S. Application Data

(63) Continuation-in-part of application No. 09/302,423, filed on Apr. 30, 1999, now Pat. No. 6,368,333, which is a continuation-in-part of application No. 09/099,523, filed on Jun. 18, 1998, now Pat. No. 6,306,147, which is a continuation-in-part of application No. 08/496,470, filed on Jun. 29, 1995, now Pat. No. 5,810,842, and a continuation-in-part of application No. 08/797,909, filed on Feb. 10, 1997, now Pat. No. 6,120,512.

(30) Foreign Application Priority Data

Jun. 29, 1994 (IT) ............................... FI94000131
Feb. 10, 1996 (IT) ............................... FI96000108

(51) Int. Cl.
*A61B 17/50* (2006.01)

(52) U.S. Cl. ................................................. 606/131

(58) Field of Classification Search ................. 606/131; 604/416, 289
See application file for complete search history.

(56) References Cited

U.S. PATENT DOCUMENTS

| 5,318,556 A * | 6/1994 | Avallone et al. ............ 604/410 |
| 6,080,165 A | 6/2000 | DeJacma |
| 6,139,554 A | 10/2000 | Karkar et al. |
| 2001/0027324 A1 | 10/2001 | Bernabei et al. |
| 2002/0016601 A1 | 2/2002 | Shadduck |

FOREIGN PATENT DOCUMENTS

| GB | 1444985 | 8/1973 |
| IT | 01286939 | 3/1996 |

* cited by examiner

*Primary Examiner*—Michael Thaler
(74) *Attorney, Agent, or Firm*—Foley & Lardner LLP

(57) ABSTRACT

A dermabrasion apparatus operates by a flow of air and reducing substances conveyed to a patient through a handpiece. The apparatus includes an oval-shaped mixing bottle that has a first enclosed region for holding reducing substances. The mixing bottle includes a cap that has two tubes extending therefrom, for coupling to respective input and output legs of the handpiece. The mixing bottle also includes a second enclosed region for holding one of the two tubes that provides an air-tight coupling between the output leg of the handpiece and a collecting bottle. The mixing bottle is oval-shaped so that a user can readily manipulate the handpiece so as to move the handpiece coupled to the mixing bottle in a desired direction. This is especially useful for small handpieces that are hard to hold onto by themselves.

15 Claims, 14 Drawing Sheets

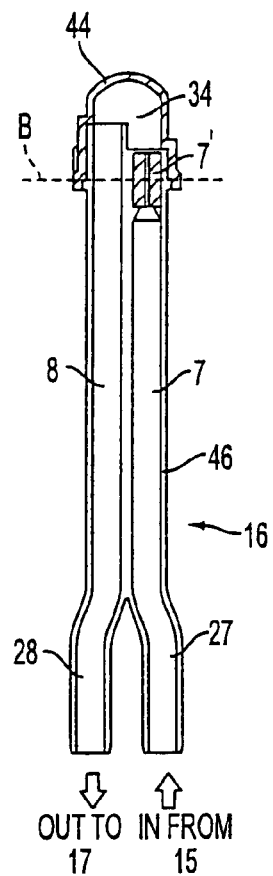
FIG. 6
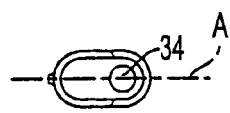
FIG. 7
 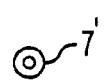
FIG. 8A   FIG. 8B

DERMABRASION APPARATUS AND METHOD HAVING OVAL-SHAPED MIXING BOTTLE

RELATED APPLICATIONS

The present application is a continuation-in-part of U.S. Ser. No. 09/302,423 filed Apr. 30, 1999, now U.S. Pat. No. 6,368,333, which itself is a continuation-in-part of U.S. Ser. No. 09/099,523 filed Jun. 18, 1998, now U.S. Pat. No. 6,306,147, which itself is a continuation-in-part of U.S. Ser. No. 08/496,470 filed Jun. 29, 1995, now U.S. Pat. No. 5,810,842, and U.S. Ser. No. 08/797,909 filed Feb. 10, 1997, now U.S. Pat. No. 6,120,512, all of which are incorporated in their entirety herein by reference.

BACKGROUND OF THE INVENTION

A. Field of the Invention

The present invention relates to the field of the cosmetic and microsurgical treatments. In particular, the present invention relates to a microdermabrasion method and apparatus and to the components making up the apparatus, operating by a pressurized flow of air and reducing substances, preferably corundum.

B. Description of the Related Art

Several technical solutions to produce a microdermabrasion apparatus are already known, all comprising vacuum means and/or pressurizing means which send a flow of air and reducing substances on a tissue portion to be treated and then remove from that portion the abraded particles. A drawback of such systems is that the sterility of the various components is not guaranteed, without the use of complicated and expensive processes.

Italian patent application FI194A000131, which corresponds to U.S. application Ser. No. 08/496,470 and is incorporated in its entirety herein by reference, describes a dermabrasion apparatus operating by a flow of reducing substances. The apparatus comprises a compressor, a vacuum pump, and three detachable one-piece components. The components include a mixing bottle, a collecting bottle for the abraded particles and a handpiece to touch the tissue to be treated. These components are preferably made of glass or plastic material and can be easily sterilized.

However, potential drawbacks of such an apparatus include the fact that the air pressurization is performed by a compressor placed inside the apparatus, making it necessary to sterilize the air because, during treatment, the compressor could be infected by bacteria which would be afterwards conveyed on the patient's skin by the pneumatic system. Furthermore, while the above-mentioned one-piece components are sterilized after the apparatus has been used, they do not guarantee proper sterility when the apparatus performs succeeding treatments on different patients. A further drawback is that contamination can occur when the mixing bottle is filled with new reducing substances or when the collecting bottle is cleaned of the abraded particles.

SUMMARY OF THE INVENTION

According to one aspect of the invention, there is provided an apparatus for use in dermabrasion, which includes a mixing bottle having an oval shape. The mixing bottle is configured to be attached to a handpiece, and the mixing bottle is configured to be held and moved by an operator during a dermabrasion treatment, to thereby move the handpiece in a desired manner.

According to another aspect of the invention, there is provided an apparatus for use in dermabrasion, which includes a first enclosed region for holding reducing substances to be applied to a patient during a dermabrasion treatment. The apparatus also includes a cap that includes a first port and a second port, the cap defining a top surface of the first enclosed region. The apparatus further includes a first tube that is configured to fit within the first port and into the first region, one end of the first tube extending out from the first port. The apparatus still further includes a base defining a bottom surface of the first enclosed region. A handpiece is configured to couple to the first and second ports so as to be moveable is a same manner and direction as the apparatus.

According to yet another aspect of the invention, there is provided a method of dermabrading skin of a patient using a dermabrasion apparatus that includes a handpiece and a mixing container. The method includes attaching the handpiece to the mixing container. The method also includes grasping the mixing container. The method further includes moving the mixing container in order to thereby move the handpiece attached thereto to desired locations of the skin of the patient.

According to still another aspect of the invention, there is provided a mixing bottle for use in dermabrasion. The mixing bottle includes a top portion having at least a first opening and a second opening. The mixing bottle also includes a first enclosed region in which a collecting tube is provided therein, the collecting extending through the first opening. The mixing bottle further includes a second enclosed region in which a mixing tube is provided therein, the mixing tube extending through the second opening. The mixing bottle still further includes a bottom portion having at least a first opening in which the collecting tube extends therethrough. The collecting tube provides an air-tight coupling between a handpiece and a collecting bottle, and the mixing tube provides an air/reducing substances mixture from the second enclosed region of the mixing bottle to the handpiece, to be provided to a skin region of a patient by way of the handpiece. According to still another aspect of the invention, there is provided a mixing bottle for use in dermabrasion. The mixing bottle includes a top portion having at least a first opening and a second opening. The mixing bottle also includes an enclosed region in which a mixing tube is provided therein, the mixing tube extending through the second opening. The mixing bottle further includes a bottom portion having at least a first opening in which a collecting tube extends therethrough. The collecting tube provides an air-tight coupling between a handpiece and a collecting bottle, and the mixing tube provides an air/reducing substances mixture from the enclosed region of the mixing bottle to the handpiece, to be provided to a skin region of a patient by way of the handpiece.

BRIEF DESCRIPTION OF THE DRAWINGS

The foregoing advantages and features of the invention will become apparent upon reference to the following detailed description and the accompanying drawings, of which:

FIG. 6 shows a first configuration of the contacting handpiece according to the invention, FIG. 7 shows a top view of the handpiece of FIG. 6;

FIGS. 8a, 8b show different views of the abrasion-proof block of the handpiece of FIG. 6;

DETAILED DESCRIPTION OF THE PREFERRED EMBODIMENTS

Figure 1:
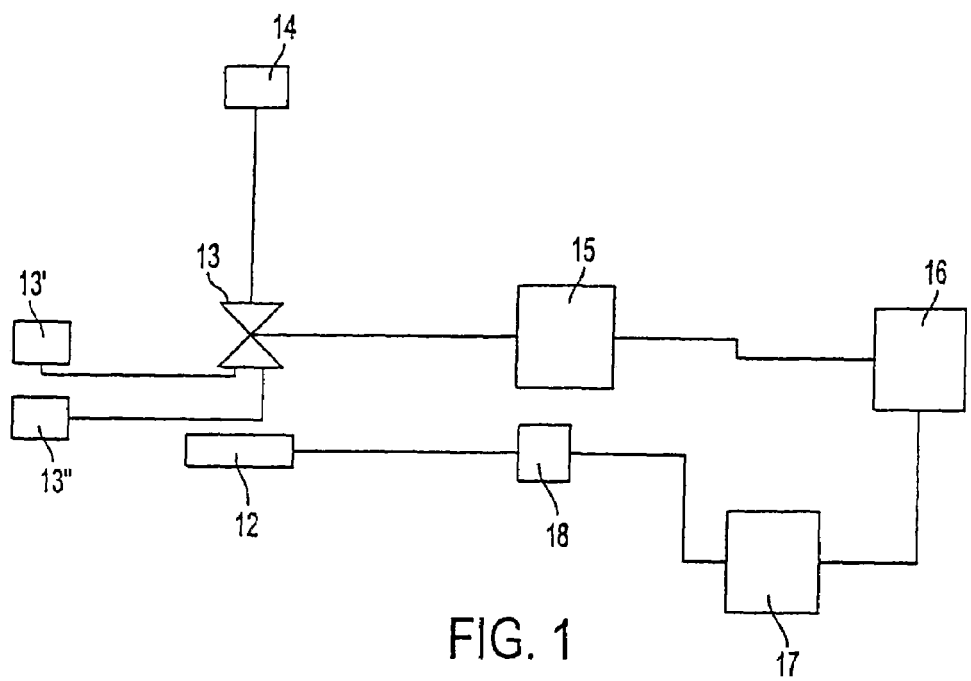
FIG. 1 schematically shows the layout of the apparatus according to a first embodiment of invention.
Figure 2:
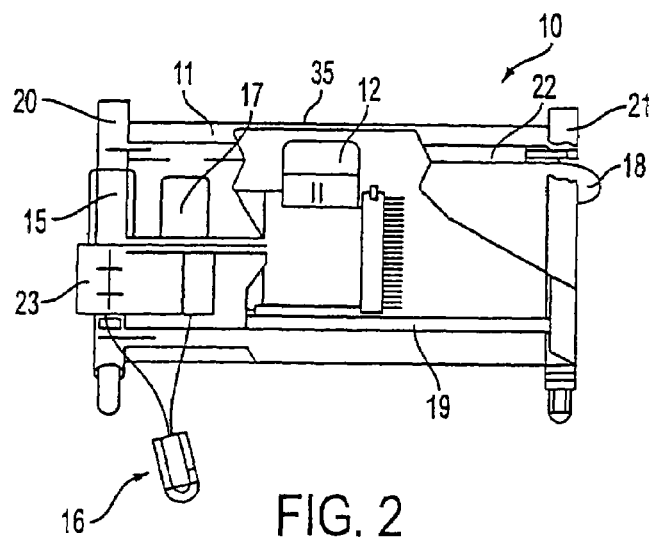
FIG. 2 shows a side view of the apparatus according to the first embodiment of the invention.

Referring to FIGS. 1 and 2, a microdermabrasion apparatus 10 according to a first embodiment of the invention comprises a housing 11, a vacuum pump 12, a mixing bottle 15 containing the reducing substances, for example corundum or aluminum oxide (sand-like substance), and a collecting bottle 17 to collect the reducing substances and the abraded tissue particles after use. As shown in FIG. 1, apparatus 10 is connected by a pneumatic system to a handpiece 16, which is intended to contact the tissue portion (e.g., skin of a patient) during treatment of a patient. The first embodiment also provides a valve 13 controlled by a switch 14, for example a treadle or a hand-operated switch, able to switch the air inlet from two different sources 13', 13". In a first example, the first source is a bottle of pressurized and sterilized air, and the second source is air at ambient pressure. In another possible configuration, the switching operates between two pressurized bottles feeding the sterilized air at different levels of pressure, so that a user can vary the abrasion efficiency of the apparatus according to the treatment requirements without interrupting the treatment. The same effect can be achieved by providing a single source with two outlet connections adjusted to output the air at different pressures. Downstream from the collecting bottle 17 and upstream from the vacuum pump 12, there is also provided a filter 18 to stop small particles flowing accidentally from the collecting bottle 17. The filter 18 is an optional component, depending upon the degree of sterility desired.

Figure 3:
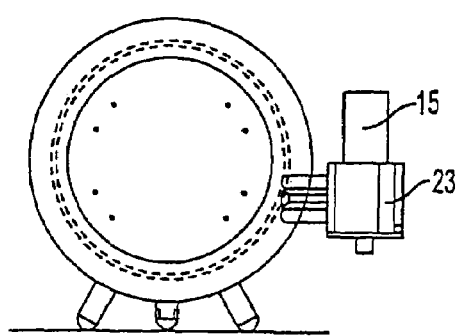
FIG. 3 shows a front view of the apparatus of FIG. 2.
Figure 4:
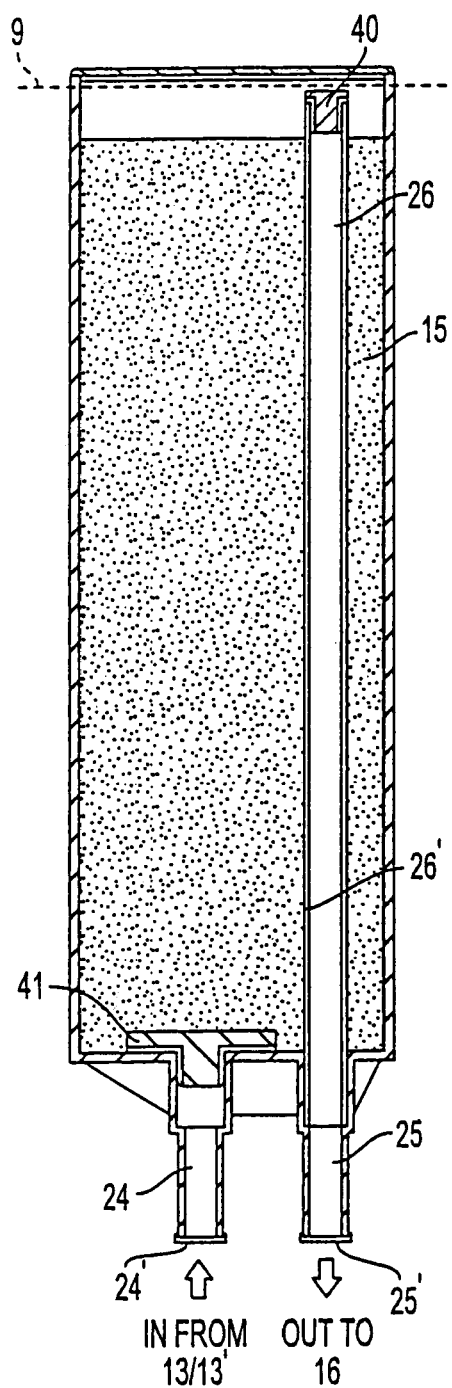
FIG. 4 shows a first configuration according to the invention of the mixing bottle filled with reducing substances.

FIG. 2 and FIG. 3 illustrate a preferred construction of the housing 11, which includes a casing 35, preferably made of plexiglass, and a bar 19 supporting the vacuum pump 12, where lateral flanges 20, 21 are connected by a threaded tie rod 22. Housing 11 further includes a tray 23, preferably an external tray, fixed to the flange 20 and housing the mixing bottle 15 and the collecting bottle 17. The tray 23 is preferably made of metal or plastic. Flange 21 holds the filter 18 placed upstream from the vacuum pump 12. Referring to FIG. 4, the mixing bottle 15 is a substantially cylindrical one-piece block obtained, for example, by ultrasound welding along a horizontal junction line 9. In FIG. 4, the junction line 9 is shown near the top portion of the mixing bottle 15, to allow for simpler manufacturing of the pieces making up the mixing bottle 15. Of course, the junction line 9 can be placed at any other location of the mixing bottle 15, while remaining within the scope of the invention. Alternative the mixing bottle 15 may be made from a one-piece construction, without any welding of sections required.

Mixing bottle 15 is provided with connection pipes 24, 25 connected respectively with valve 13, and with the pneumatic duct leading to the handpiece 16 according to the scheme of FIG. 1. Pipe connection 25 extends into the mixing bottle 15 with a suction tube 26 having a hole 26' (or aperture) near the bottom wall of mixing bottle 15, through which the reducing substances are introduced into the pneumatic system. Preferably, hole 26' is located at a position between 1/10 and 3/10 of the total height of the mixing bottle. This position of the hole 26' is high enough on the pipe connection 25 such that an air/corundum mixture that passes through the hole 26' and thereby into the pipe connection 25 is of sufficient density so as not to cause blockage of the hole 26'. Also, the position of the hole 26' is low enough on the pipe connection 25 such that air introduced into the mixing bottle 15 causes sufficient vibration or movement of the corundum inside the mixing bottle 15, so as to create a desired air/reducing substances (or 'air/cordundum') mixture.

Figure 9A:
FIG. 9a shows one of the filters (or labyrinths) of the mixing bottle of FIG. 4.
Figure 9B:
FIG. 9b shows the other of the filters (or labyrinths) of the mixing bottle of FIG. 4.

Tube 26 and the inner end of the pipe connection 24 are provided with labyrinths 40, 41 schematically shown in FIGS. 9a, 9b, respectively. Labyrinths 40, 41 present a T section with radial passages through which the air can pass whereas there is avoided the accidental backflow of the corundum through the pipe 24 connection and the possible introduction of the same into the tube 26, during the transporting operation. Preferably, labyrinths 40, 41 have eight passages (or holes) symmetrically spaced on the top portion of thereof. Other numbers of passages may be envisioned while remaining within the scope of the invention. Each passage preferably has a diameter of about 1 millimeter, so as to provide air bubbles of a size that causes sufficient vibration and movement of the corundum within the mixing bottle 15. The air bubbles output from each hole of labyrinth 41 move upwards as streamlets of air, and cause vibratory movement of the corundum. The T-shape of the labyrinth 41 is structured such that, during non-operational states (i.e., when the hole 34 is uncovered), the corundum in the mixing bottle 15 only moves part-way into the top-T portion of each T-shape passage, and does not move into the bottom-T portion of each passage. This is due primarily to the non-fluidity of the corundum, which tends to bunch up like sand and not flow readily unless provided with air under pressure. Thus, back-flow of the corundum into the connection tube 24 is effectively prevented.

According to the first embodiment of the invention, the mixing bottle 15 is filled with the corundum in an aseptic (sterilized) environment and thereafter is preferably by ultrasound welding, and then sealed by suitable plug 24', 25'. In the one-piece, non-welded configuration, the corundum is placed into the mixing bottle, and then the mixing bottle is sealed by plugs 24', 25'. For example, each plug 24', 25' can have a bottom rubber layer which is pierced by the extremities of corresponding connecting junctions of the external tray 23 when the plugs 24', 25' are fitted into the external tray 23. Alternatively, each plug 24', 25' may comprise an aluminum foil or strip, which is punctured when the mixing bottle 15 is fitted into the external tray 23. In such a way, the mixing bottle 15 is connected with the valve 13 and with the downstream handpiece 16.

Figure 10:
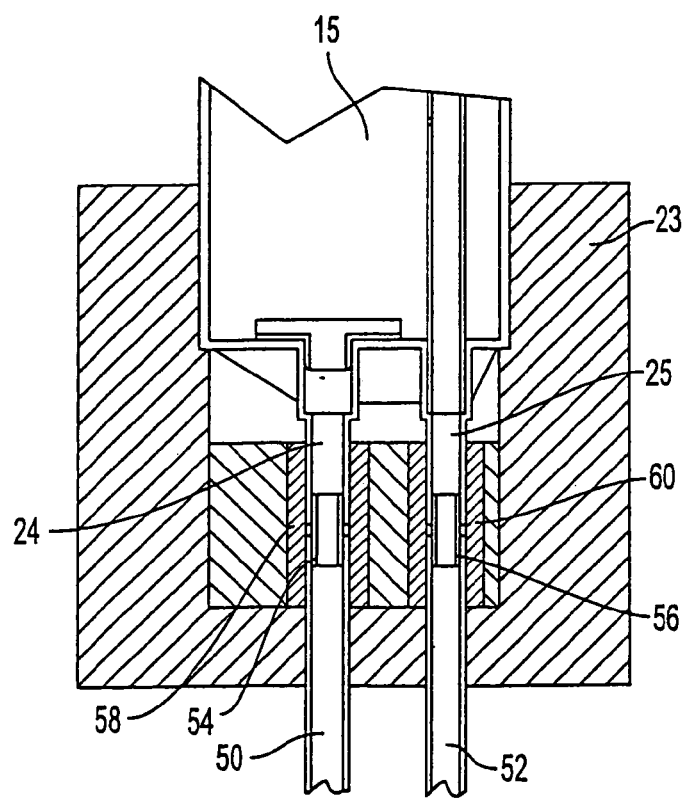
FIG. 10 shows the fitting of the mixing bottle onto the external tray according to the present invention.

FIG. 10 shows the fitting of the mixing bottle 15 onto the external tray 23. In FIG. 10, the external tray 23 includes two connection pipes 50, 52, which are preferably made of a silicone-based material, or plastic. Pipes 50, 52 are flexible and preferably transparent in color. Disposed inside pipes 50, 52 are metal rings 54, 56, respectively. Disposed outside pipes 50, 52 are rubber seals 58, 60 which are snugly fit around pipes 50, 52. Rubber seals 58, 60 provide a strong air-tight seal when connection pipes 24, 25 are fitted against pipes 50, 52, respectively. When mixing bottle 15 is fitted onto external tray 23, the connection pipes 24, 25 are moved downward towards the pipes 50, 52, so as to cause piercing of the plugs 24', 25' by metal pipes 54, 56. That way, an air-tight connection is provided.

Referring to FIG. 6, the handpiece 16 according to a first configuration comprises a substantially elliptical one-piece block having the upper portion in the shape of a hollow elliptical cap 44. Handpiece 16 is provided with an inlet connection 27 corresponding to an inner tube 7 through which the air and the reducing substances enter into the elliptical cap 44. After use, the reducing substances are removed from the elliptical cap 44 by a second tube 8 and a corresponding outlet connection 28. The handpiece elliptical cap 44 presents an opening 34, the rim of which defines the patient's tissue portion impinged upon by the reducing substances ejected from tube 7. In the preferred embodiment, the opening 34 is angled such that the air/reducing substances mixture is provided to the patient's tissue at an angle of approximately 45 degrees. That way, there is less of a chance that the air/reducing substances adheres or clings to the skin left on the patient during treatment. For example, if the air/reducing substances mixture was provided to the patient at an angle of 90 degrees (i.e. in a direction straight into the tissue of the patient), then some of the mixture may lodge into the skin (dermis) of the patient, and not cause the desired "brushing" against the skin of the patient that the 45 degree angle approach provides. This adherence of the mixture to the patient's skin is generally undesirable, and may result in infection to the patient if not removed antiseptically. However, for some purposes, applying the mixture at an angle of 90 degrees may be suitable, and the present invention may be utilized with handpieces that provide the mixture at such an angle.

According to the first configuration of the handle according to the invention the upper end of tube 7, which is the part subjected to the highest abrasion, is provided with an insert block 7', shown in FIGS. 8a, 8b. Block 7' is a cylinder having an internal diameter smaller than a diameter of the tube 7 to achieve a smaller flow area and thus increase the flow rate of the reducing substances. Block 7' is made of a hard material, preferably glass or ceramic. In a first embodiment, handpiece 16 has two half parts 46 symmetrical with respect to line A of FIG. 7 and manufactured, for example, by injection molding, together with the corresponding half parts of tubes 7, 8. Before assembling, block 7' is inserted into the upper end portion of tube 7 and the spherical cap 44 is attached so that the opening 34 corresponds to the block 7'. That is, an air/corundum mixture output from mixing bottle 15 goes through inlet connection 27, through inner tube 7 and then through insert block 7', and finally contacts a patient's skin (not shown) covering opening 34. The covering of the opening 34 creates a vacuum, so as to cause the air/corundum mixture to flow towards the patient's skin. The air/corundum mixture under pressure causes abrasion of the patient's skin, and a skin/corundum/air mixture is passed through tube 8, through outer connection 28, and is collected by collecting bottle 17. After attachment of the elliptical cap 44, the assembly is closed, for example by ultrasound welding along line A and line B between the elliptical cap 44 and the lower body 46 (see FIGS. 6 and 7). Alternatively, the elliptical cap 44 is welded to the lower body 46 by a single injection molding operation. In the alternative configuration, the handpiece 16 corresponds to a unitary piece or monoblock, such as the U-shaped mono-block shown in FIG. 6 of the drawings, or the one shown in FIGS. 7 and 8 of U.S. Pat. application Ser. No. 08/496,470.

Figure 11:
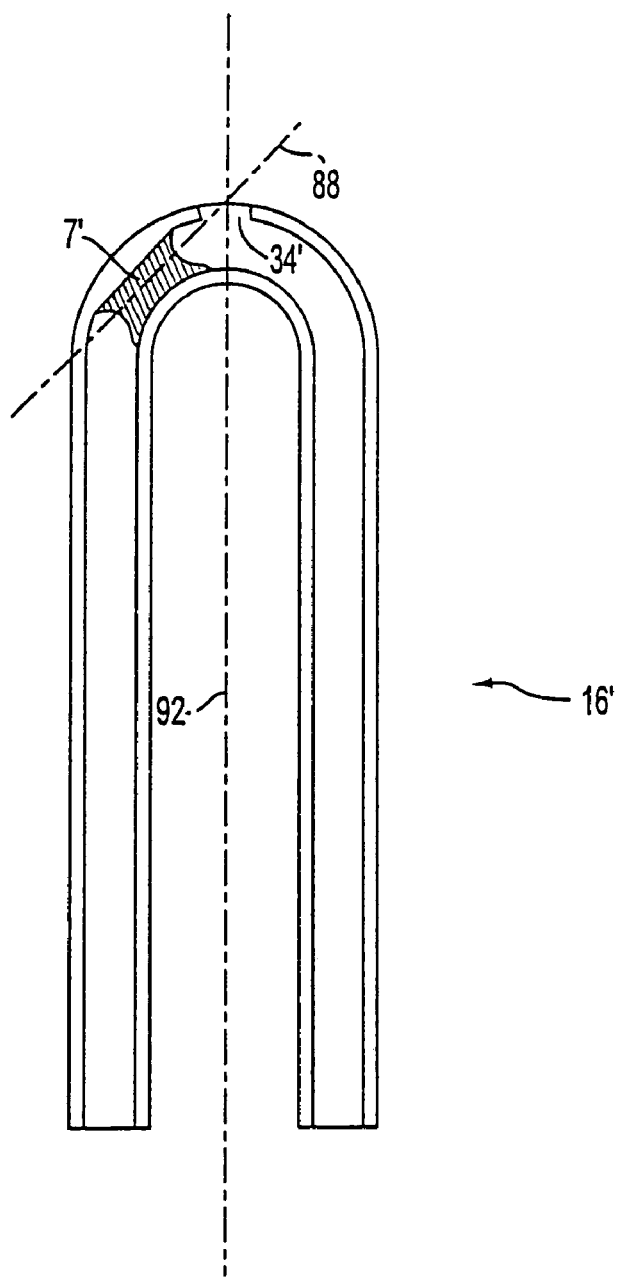
FIG. 11 shows another configuration of the contacting handpiece according to the present invention.
Figure 12:
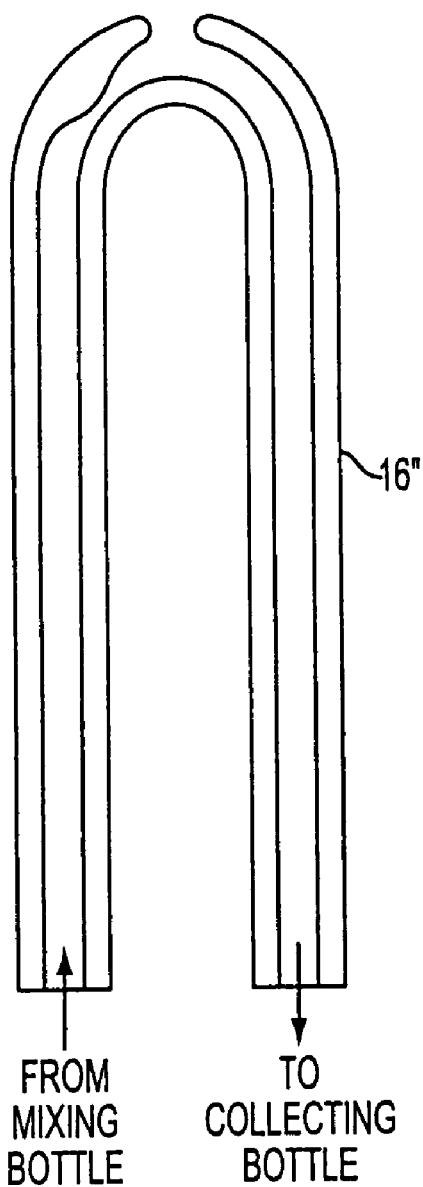
FIG. 12 shows yet another configuration of the contacting handpiece according to the present invention.

In a second configuration of the handle, as shown in FIG. 11, the contacting handpiece 16' is a mono-block (single, non-separable unit) which includes an insert block 7' situated in a curved portion at the top of the handpiece 16'. By this configuration, the air output from the insert block 7' is directed towards the opening 34', with the air direction being shown by the dashed line 88. The opening 34' is positioned at a substantially central position of the handpiece 16'. A longitudinal axis of the handpiece 16' that bisects the handpiece 16' is shown by dashed line 92. In the second configuration of the handpiece, the handpiece 16' is manufactured as a single piece (except of course the insert block 7'), without the need for combining sections to thereby form the handpiece. In a third embodiment, the insert block 7' may be omitted, and instead the handpiece 16" may be formed such that the location where the insert block 7' is located in the second configuration is made narrower than other portions of the handpiece 16", as shown in FIG. 12.

Figure 5:
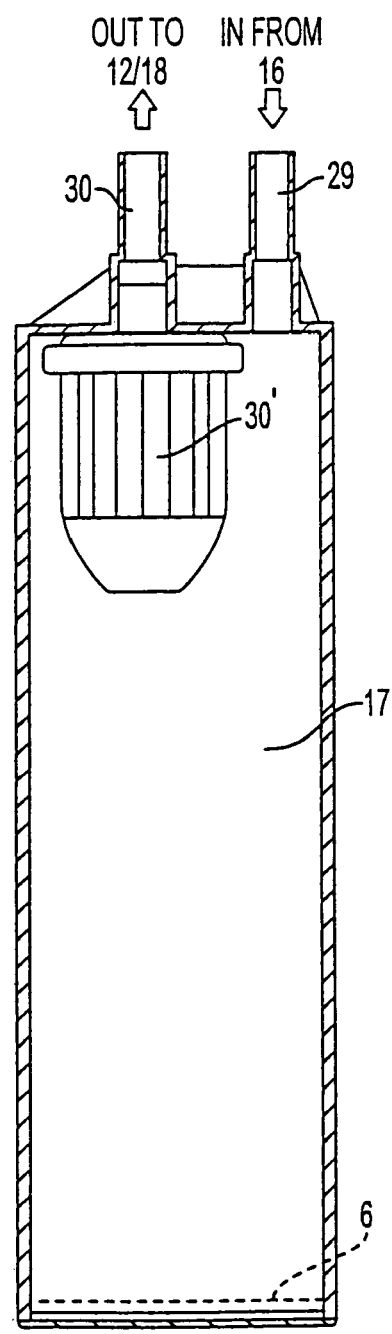
FIG. 5 shows a first configuration of the collecting bottle according to the invention.

Referring to FIG. 5, there is shown a first configuration of the collecting bottle 17, placed downstream of the handpiece 16 and upstream of the vacuum pump 12, according to the pneumatic system scheme of FIG. 1. In this first configuration, the collecting bottle 17 has a cylindrical hollow one-piece block provided with two upper connections 29, 30, the first operating as inlet for the reducing substances from handpiece 16, the second as a passage for the air aspirated by vacuum pump 12. Connection 30 is provided with an air filter 30' in order to avoid the passage of used reducing substances and of tissue abraded particles towards the vacuum pump 12.

Collecting bottle 17 is preferably assembled by welding (preferably ultrasound welding) along line 6, the upper portion including connections 29, 30. The welding is preferably to connect a small portion of the collecting bottle 17 to the rest of the collecting bottle 17. That way, it is easier to manufacture the two pieces making up the collecting bottle 17. Downstream from the collecting bottle 17 is disposed a filter 18 for filtering small particles passed through the filter 30' and conveyed towards vacuum pump 12. Filter 18 is preferably disposed immediately downstream from collecting bottle 17. Advantageously, the connections of collecting bottle 17 and handpiece 16 are provided with plugs, similar to previously described plugs 24', 25' which are intended to seal both collecting bottle 17 and handpiece 16 until their initial use, and to allow a quick and easy connection to the pneumatic system. In a second configuration, the collecting bottle may be made from a single-piece (mono-block) construction, without the need for welding of sections.

Figure 13:
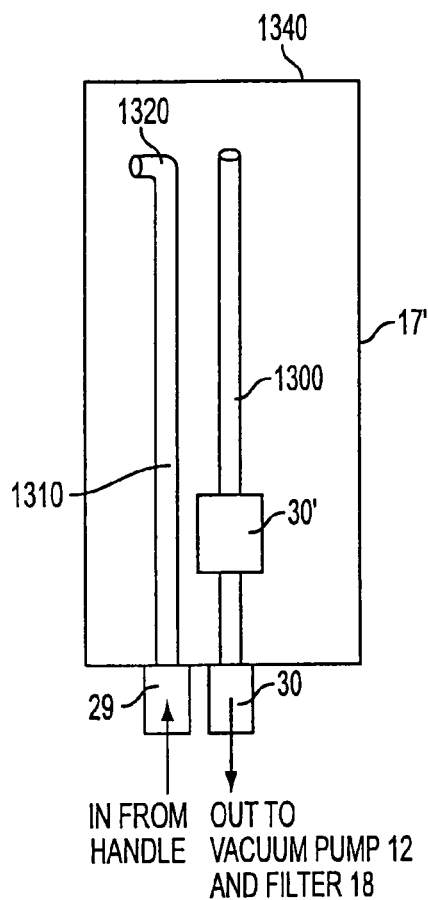
FIG. 13 shows another configuration of the collecting bottle according to the present invention.

FIG. 13 shows a collecting bottle 17' according to a second configuration, which may be constructed as either a mono-block or by welding of sections (as in the first configuration). In FIG. 13, the collecting bottle 17' is configured such that it is placed onto the tray 23 with the plug-side down (e.g., in the orientation as shown in the figure). To accommodate such a placement of the collecting bottle 17', the tube 1320 that provides the air/reducing substances/abraded tissue mixture to the inside of the collecting bottle 17' is made almost as long as the length of the collecting bottle 17'. The tube 1320 is preferably at least 80% the length of the collecting bottle 17'.

In the second configuration, the collecting bottle preferably has a radius of about 2.5 cm, and a length of about 7 cm, but of course other sizes are possible. The tube 1320 ends at a position within a few millimeters of the top surface 1340 of the collecting bottle 17'. Also, the tube 1300 (also called "suction tube" hereinbelow) that provides the suction from the vacuum pump 12 to the collecting bottle 17' (and thereby to the handle) is made almost as long as the length of the collecting bottle 17'. Again, the length of the tube 1300 is preferably at least 80% of the collecting bottle 17'. Furthermore, the suction tube 1300 is positioned such that its top-most, receiving end is located at a central position within the cylindrically-shaped collecting bottle 17'. This can be done by either positioning the connection 30 such that it is located at a central position on the bottom of the collecting bottle 17' and then providing a tube 1300 that is straight. Alternatively, this can be done by positioning the connection 30 at another, non-central location, and then utilizing a non-straight tube 1300 that has its end portion located at a substantially central location near the top of the collecting tube 17'.

Figure 14:
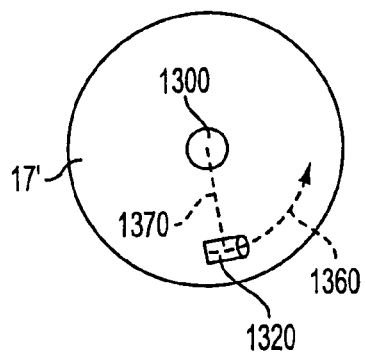
FIG. 14 shows a top view of the other configuration of the collecting bottle according to the present invention.

Referring now to FIG. 14, the tube 1310 has a 90 degree bent portion 1320 at the top of the tube 1310, where that bent portion 1320 is positioned about 2 mm away from the outer periphery of the collecting bottle 17. With this configuration, the air/reducing substances/abraded tissue mixture exits the bent portion 1310 of the tube 1320 and moves in a direction tangential (or substantially tangential) to a circumference of the cylindrical collecting bottle 17'. In other words, the bent portion 1320 is positioned such that it is substantially perpendicular to an imaginary line 1370 that is drawn to the center of the cylindrical collecting bottle 17'. With this second configuration, the air/reducing substances/abraded tissue mixture comes out of the bent portion 1320 of the tube 1310 in such a manner that the reducing substances/abraded tissue portion of that mixture follows the periphery of the collecting bottle 17', to thereby create a vortex, and thereby makes its way down to the bottom of the collecting bottle 17'. The kinetic energy of the air/reducing substances/abraded tissue mixture, as it comes out of the bent portion 1320, is such that the kinetic energy is converted to a centrifugal force that makes the reducing substances/abraded tissue portion of the air/reducing substances/abraded tissue mixture follow a path close to the periphery of the cylindrical collecting bottle 17' all the way down to the bottom portion of the collecting bottle 17', where that mixture comes to rest. As such, the reducing substances/abraded tissue portion of the mixture does not come into contact with the middle portion of the collecting bottle 17' as it makes its way down to the bottom of the collecting bottle 17'. This lessens the possibility that the filter 30' will become clogged due to the reducing substances/abraded tissue adhering to it. Also, this lessens the possibility of the reducing substances/abraded tissue entering the vacuum hole at the top portion of the tube suction 1300.

The kinetic energy is not strong enough to maintain the air along the outer periphery path 1410 (see FIG. 15), but rather the air, being of course lighter than either the reducing substances or the abraded tissue, is sucked into a central location of the collecting bottle 17' where the suction tube 1300 is positioned, and thereby makes its way through the suction tube 1300 and towards the vacuum pump 12. With such an approach, and with the filter 30' preferably located at a position such that it will not come into contact with the reducing substances/abraded tissue mixture (e.g., positioned a few centimeters above the bottom portion of the collecting bottle 17', clogging to the filter 30' will not occur.

Figure 15:
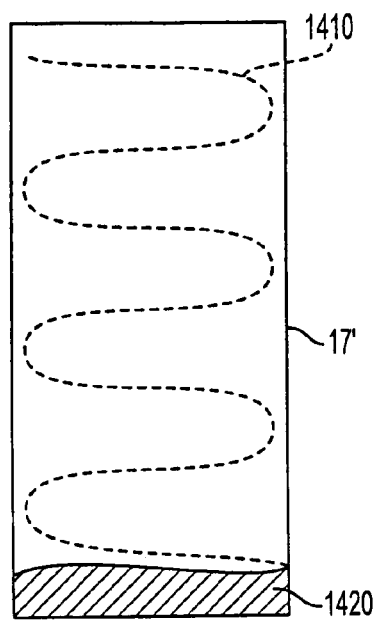
FIG. 15 shows a path of reducing substances/abraded tissue within the other configuration of the collecting bottle according to the present invention.

In an alternative configuration of the collecting bottle 17', the filter 30' may not be provided at all, since the reducing substances/abraded tissue mixture will not be directed to the vacuum tube 1300 by way of the configuration of the vacuum tube 1300 and the tube 1310 (and its bent portion 1320). FIG. 15 shows a path 1410 of the air/reducing substances/abraded tissue mixture as it leaves the bent portion 1320 of the tube 1310 and makes its way down, as a vortex following the shell of the collecting bottle 17', down to the bottom portion of the collecting bottle 17', where it comes to rest as reducing substances/abraded tissue mixture 1420. The vortex separates the air of the air/reducing substances/abraded tissue mixture from the reducing substances/abraded tissue portion, as the reducing substances/abraded tissue portion follows the periphery of the collecting bottle (see line 1410 of FIG. 15) as the air is sucked into the central portion where the suction tube 1300 is located (see FIG. 13 and FIG. 14).

After manufacture, the mixing bottle, the collecting bottle and the handpiece can be packaged, individually or in a kit including either all three components or at least the handpiece and collecting bottle, in sterilized packaging. The connection tubes can optionally be included in the kit. By having a disposable mixing bottle 15 that is manufactured and sent with seals 24', 25' to a user or operator, the user does not have to worry about bacteria or the like entering the mixing bottle 15, since it has already been sterilized (by gamma rays, for example) during manufacturing. Also, each mixing bottle may also have a silica-gel package or other type of desiccant disposed within the mixing bottle along with the corundum. The silica-gel package keeps any moisture from forming inside the mixing bottle, thereby keeping the corundum from clumping up and causing problems in the system. That way, a heating element to keep the corundum dry inside the mixing bottle is not required in the present invention.

The one-piece blocks according to the invention constitute a kit of disposable components which does not require the steps of: filling the mixing bottle with the reducing substances, cleaning the abraded particles from the collecting bottle and handpiece, or sterilizing critical parts of the apparatus. These steps were required in conventional devices, and represented additional time and money spent to achieve treatment safety. In the present invention, it is also possible to set an expiration time for the sterility condition of the blocks individually or as contained in the unique kit packaging. Upon reaching the expiration time, all critical parts of the apparatus can be safely and quickly replaced due in part to the described sealing plugs 24, 25, used to connect handpiece 16, 16', or 16" with the mixing bottle 15 and the collecting bottle 17 or 17'. Preferably, the blocks are 'single-use' blocks that are to be disposed after a single treatment of a patient.

The blocks can be made of any suitable plastic or vitreous material. A polycarbonate is preferred because it is a low cost material and can be sterilized by an autoclave when reuse of one or more components is needed. Alternatively, a polystrene structure or the like may be used. According to a further feature of the invention, the kit components can be manufactured in different colors in order to allow a better identification of their functions by the user, or can be transparent to allow the user to visually detect any contamination particles remaining after sterilization.

Furthermore, due to the disposable nature of the present invention, the mixing bottle and the handle can be manufactured as a single unit, or mono-block, without any way of removing or separating these components from each other. Since each component is to be thrown away after treatment of a patient, having a mono-block structure of a handle and mixing bottle is not a problem, since these components are not to be cleaned after treatment, but rather discarded. Such a configuration would not require a flexible tubing between the mixing bottle and the handle, but rather the entire one-piece construction can be made of ceramic or glass or the like.

Figure 16:
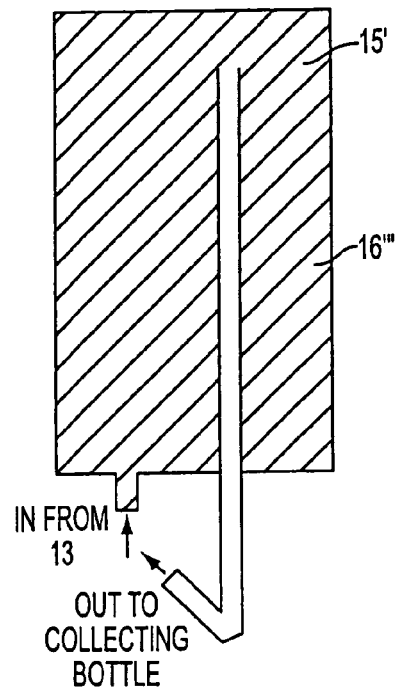
FIG. 16 shows a second embodiment of the present invention, in which a mixing bottle and handle are a single, one-piece mono-block construction.

FIG. 16 shows a second embodiment of the present invention, which is a mono-block comprising a mixing bottle and a handle. The entire structure shown in FIG. 16 is a one-piece construction, and where the mixing bottle portion 15' and the handle portion 16''' together comprise the mono-block structure. In another possible configuration, the mixing bottle, the collecting bottle and the handle all together can be manufactured as a single, mono-block structure, to be disposed after treatment of a patient. As mentioned above, since there is no need to clean each component after treatment of a patient, as is required by conventional dermabrasion apparatuses, having a mono-block structure which combines more than one element (such as a mixing bottle and a handle; or a handle and a collecting bottle; or a handle, mixing bottle, and collecting bottle), the entire mono-block structure is disposed after treatment, and thus there is no need to connect individual components together as is required for conventional dermabrasion apparatuses.

Figure 17:
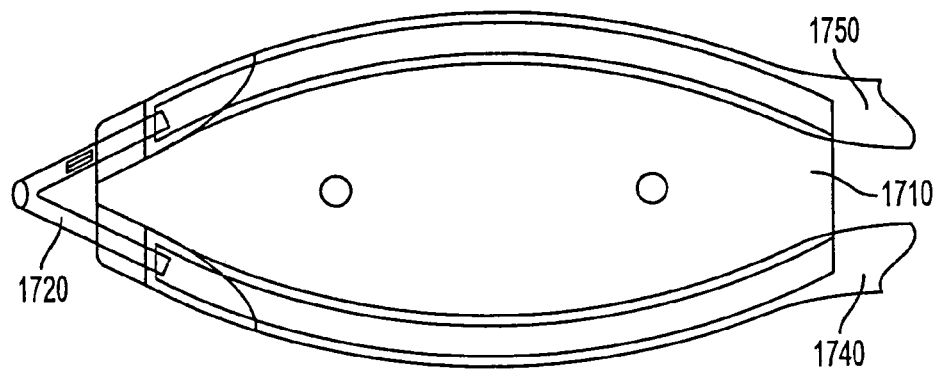
FIG. 17 shows a side view of a holding element and various items attached to it, according to a third embodiment of the invention.
Figure 18:
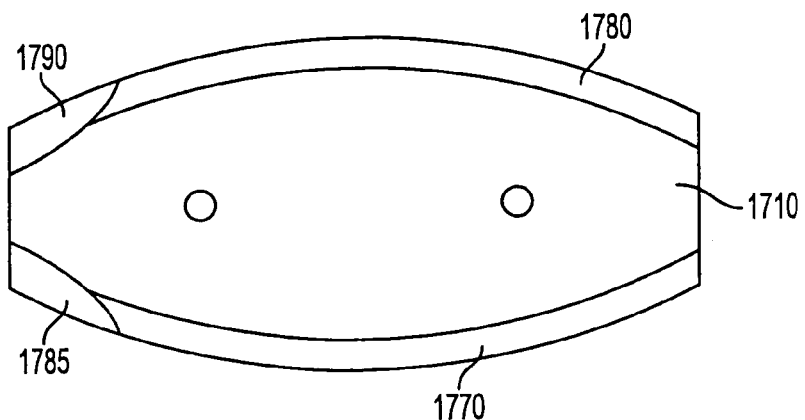
FIG. 18 shows the holding element by itself, according to the third embodiment of the invention.
Figure 19:
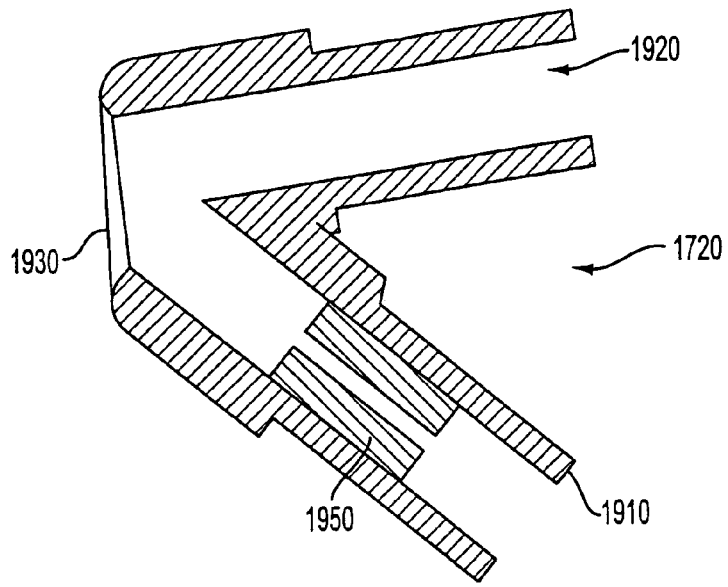
FIG. 19 shows a handpiece that can be utilized in the third embodiment.
Figure 20:
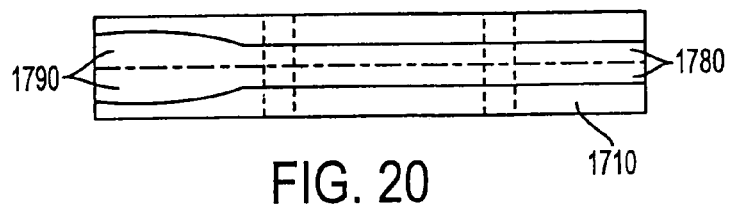
FIG. 20 shows a top view of the holding element.
Figure 21:
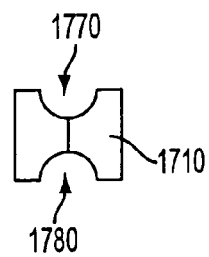
FIG. 21 shows a front-on view of the holding element.

FIG. 17 shows a side view of a holding element 1710 for a handpiece 1720, according to a third embodiment of the present invention. FIG. 18 shows a side view of the holding element 1710 by itself, and FIG. 19 shows a side view of the handpiece 1720 that is sized to be fitted onto the holding element, along with a collecting tube 1740 and a supply tube 1750. FIG. 20 shows a top view of the holding element 1710. Referring now to FIGS. 17 and 18, the handpiece 1720 is fitted onto one side of the holding element 1710, and the collecting portion 1740 and supply portion 1750 are also fitted onto the respective legs of the handpiece 1720. The groove 1770 on the top of the holding element 1710 is sized to snugly hold the collecting portion 1740 in place, by slight application of pressure (e.g., by hand typically) to fit the collecting tube within the groove 1770. FIG. 21 shows a front-on view of the holding element 1710 showing the groove 1770 and the groove 1780. The grooves 1770, 1780 are each constructed with an opening having an angle greater than 180 degrees, for example, 190 degrees, with an opening that is sized to the diameter of the respective tubes 1740, 1750. By this configuration, the collecting portion 1740 can be fitted into the groove 1770 by easy manipulation of the collecting portion 1740 into the holding element 1710. A similar approach is performed for the supply portion 1750, which is fitted into the groove 1780 on the opposite side of the holding element 1710. The grooves 1770, 1780 are preferably about 0.5 cm deep, and of course are sized to the size of the tubes 1740, 1750 that are to be fitted into the grooves.

Figure 22:
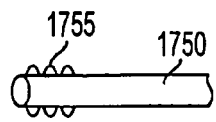
FIG. 22 shows a supply tube that can be fitted onto the holding element.

The holding element 1710 has deeper groove sections 1785, 1790 for holding the end portion of the supply and collecting portions 1740, 1750 in place. The depth of the groove sections 1785, 1790 are preferably about 0.8 cm deep, and of course are sized to the end sizes of the tubes 1740, 1750. FIG. 22 shows the supply portion or supply path 1750, which includes a larger-sized end portion 1755, and it is that end portion 1755 that is fitted into the groove section 1790, with a similar configuration for the collection tube 1740. The groove section 1790 is sized to have the larger-sized end portion 1755 snugly fit therein when pushed into the groove section 1790. The groove section 1785 is also sized to have the larger-sized end portion (not shown) of collection portion or collection path 1740 fit therein when pushed into the groove section 1785. The larger-sized end portions of the collection portion 1740 and the supply portion 1750 are sized to fit into the respective legs of the handpiece 1720.

By this configuration, the handpiece 1720 is held in place at one end of the holding element 1710, so that an operator can hold the holding piece in order to apply the small-sized handpiece 1720 to various locations on a patient's skin. Since the handpiece 1720 itself is fairly small, about 2.5 cm length from the top portion to the ends of each leg, holding the handpiece by itself without the aid of the holding element is relatively difficult. The holding element 1710, which is about 10 cm wide and about 5 cm high at its middle section, allows the operator to make precise treatments to the patient's skin by holding on to the holding element 1710 when treating the patient. As shown in FIG. 17, the holding element 1710 tapers to about a 2 cm height at its respective left and right sides, and has a maximum height at its middle portion.

Referring now to FIG. 20, the holding element 1710 is preferably constructed from two separate pieces, held in place by screws 2010, 2020 and washers 2030, 2040. The dot-dash-dot line in FIG. 20 shows where the two pieces making up the holding element 1710 meet. The holding element 1710 is preferably constructed from plexiglass, plastic or other lightweight material, to allow for ease of use.

Alternatively, the holding element 1710 may be a single, unitary block that does not require screws to hold individual portions in place.

Figure 23:
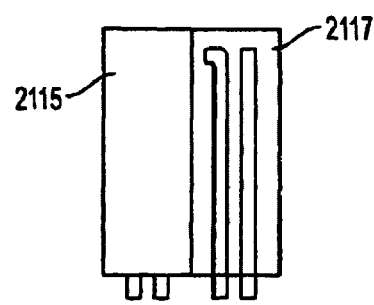
FIG. 23 shows a fourth embodiment in which a collecting bottle and mixing bottle are positioned in a same orientation.

FIG. 23 shows a fourth embodiment of the invention, in which a mixing bottle 2115 and a collecting bottle 2117 are provided as a single, unitary component, to allow for ease in inserting the mixing bottle 2115 and the collecting bottle 2117 into a tray, such as tray 23 as shown in FIG. 2. In the first embodiment of FIG. 2, the collecting bottle 17 and the mixing bottle 15 are configured to be fitted into the tray in the orientations as shown in FIGS. 4 and 5. That is, the mixing bottle 15 is to be fitted into the tray 23 with its connections 24, 25 positioned at the bottom, while the collecting bottle 17 is to be fitted into the tray 23 with its connections 29, 30 positioned at the top. However, by utilizing the structure of the collecting bottle 17' of FIG. 13, the collecting bottle 17' can also be fitted into the tray 23 in a manner like the mixing bottle, that being with its connections positioned at the bottom (in the orientation as shown in FIG. 13). As such, the mixing bottle and the collecting bottle can be fitted into the tray at the same time using the single, unitary component structure of FIG. 23. Alternatively, the collecting bottle and the mixing bottle may be separate components, but may then be affixed to each other, such by use of a rubber band or the like, and then fitted onto the tray.

Figure 24A:
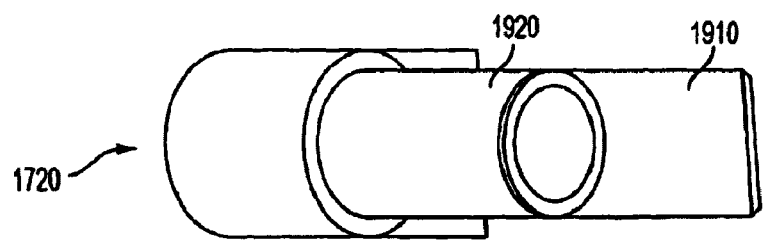
FIGS. 24a–24c show different views the handpiece according to the third embodiment, in which the air/reducing substances mixture is provided to the patient at an angle of 45 degrees.
Figure 24B:
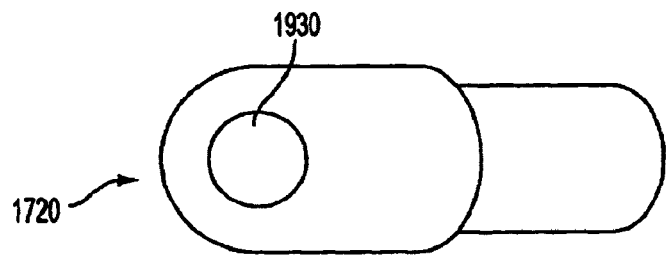
Figure 24C:
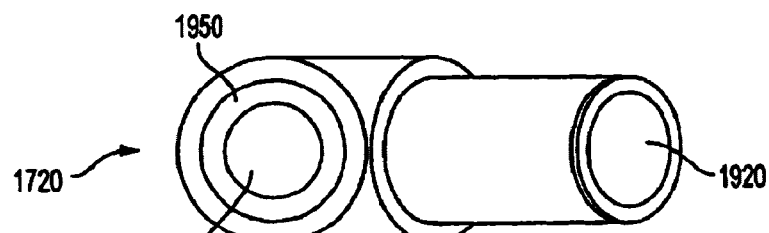

FIGS. 24a–24c show different views of the handpiece 1720 that can be fitted into the holding element 1710, or which can be utilized without the holding element 1710 in order to dermabrade the skin of a patient. FIG. 19 shows a side view of the handpiece 1710, in which the air/reducing substances mixture is applied at an angle of 45 degrees, and where a venturi 1950 (made of glass or ceramic, preferably) is positioned in the supply path 1910. The collection path 1920 is positioned at a 90 degree angle with respect to the opening 1930 that directs the air/reducing substances mixture onto a patient's skin. The collection path 1920 receives an air/reducing substances/abraded tissue mixture, where the abraded tissue corresponds to tissue from the patient's skin. The collection path 1920 receives the air/reducing substances/abraded tissue mixture by way of a suction provided on the collection path 1920. FIG. 24a shows a view along a plane in which the supply path 1910 and the collection path 1920 are both disposed. A head portion of the handpiece has a slightly greater diameter than a remaining portion of the handpiece, with the head portion being integrally formed with the remaining portion. FIG. 24b shows a view of the handpiece 1720 looking directing into the opening 1930. FIG. 24d shows the handpiece looking directly into the supply path 1910.

Figure 25A:
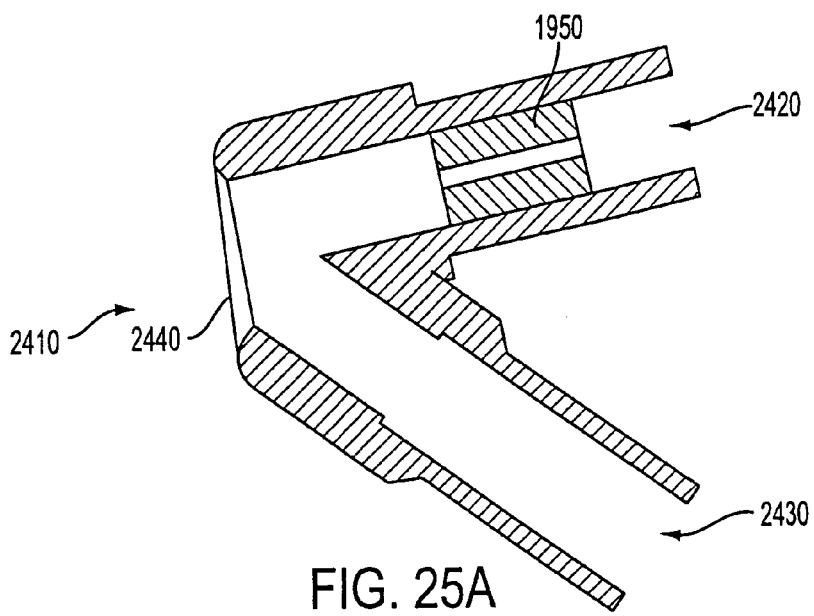
FIGS. 25a–25d show different views of another alternative configuration of the handpiece according to the third embodiment, in which the air/reducing substances mixture is provided to the patient at an angle of 90 degrees.
Figure 25B:
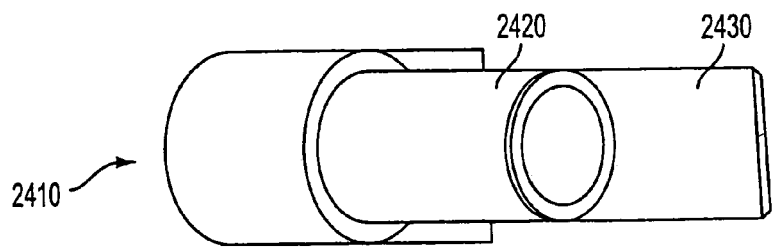
Figure 25C:
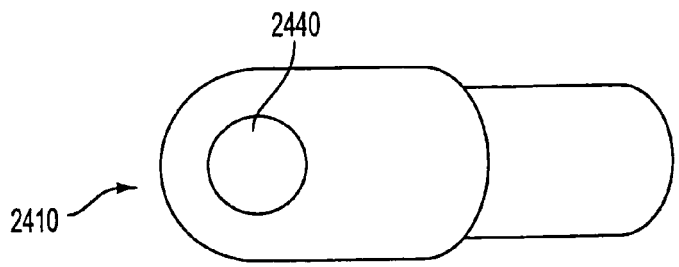
Figure 25D:
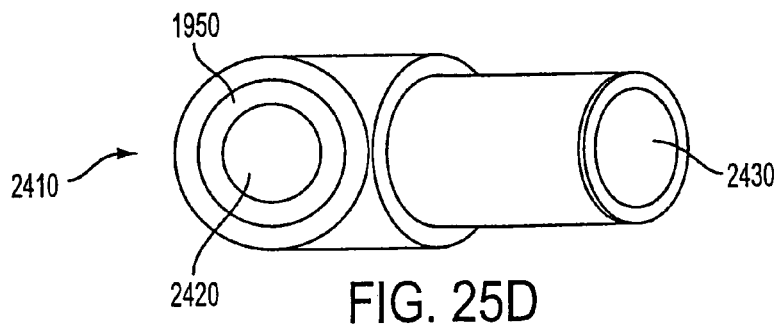

FIGS. 25a–25d show an alternative configuration of the handpiece of the third embodiment. In this alternative configuration, as seen best in the side view of FIG. 25a, a handpiece 2410 has a supply path 2420 (with a venturi 1950 fitted therein) that is positioned at a 90 degree angle with respect to the opening 2430, so as to provide the air/reducing substances mixture at an angle of 90 degrees with respect to the patient's skin. The handpiece 1720 of FIG. 19 and FIGS. 24a–24c has a collection path 1920 that receives the air/reducing substances/abraded tissue mixture at an angle of 90 degrees with respect to the patient's skin. In the alternate configuration of FIGS. 25a–25d, the handpiece 2410 has a collection path 2430 that receives the air/reducing substances/abraded tissue mixture at an angle of 45 degrees. FIG. 25b shows a view along a plane in which both the supply path 2420 and the collection path 2430 of the handpiece 2410 are disposed. A head portion of the handpiece 2410 has a slightly greater diameter than a remaining portion of the handpiece 2410, with the head portion being integrally formed with the remaining portion. FIG. 25c shows a view of the handpiece 2410 looking directing into the opening 2440. FIG. 24c shows the handpiece 2410 looking directly into the supply path 2420.

Further alternate configurations of the handpiece of the third embodiment can be contemplated while remaining within the scope of the invention, in which the collection path receives the air/reducing substances/abraded tissue mixture at an angle between 45 degrees and 90 degrees. While various configurations of a handpiece have been described with respect to the third embodiment, these handpieces may be utilized without a holding element, if desired.

The second, third and fourth embodiments may be utilized with a pressurized system, or with a compressor system, or with an aspirated system.

Figure 26:
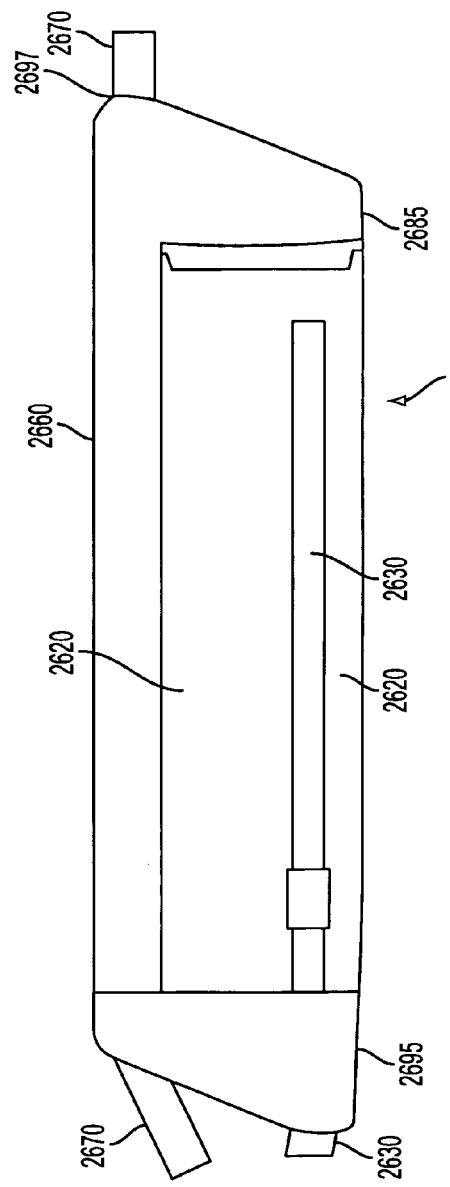
FIG. 26 shows a side view of a mixing bottle apparatus according to a fifth embodiment of the invention.
Figure 27:
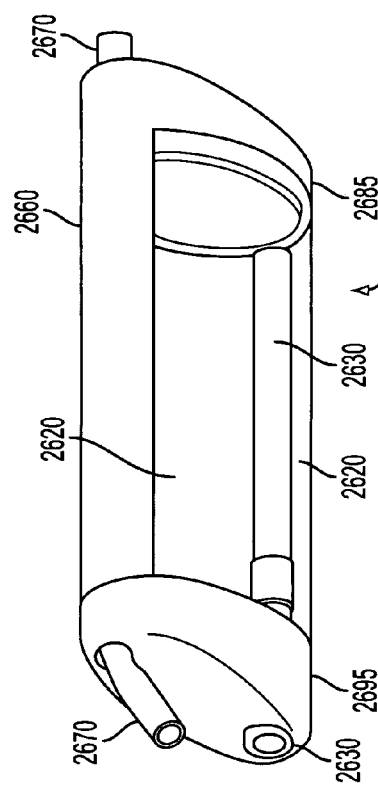
FIG. 27 shows a left-side perspective view of the mixing bottle apparatus according to the fifth embodiment of the invention.
Figure 28:
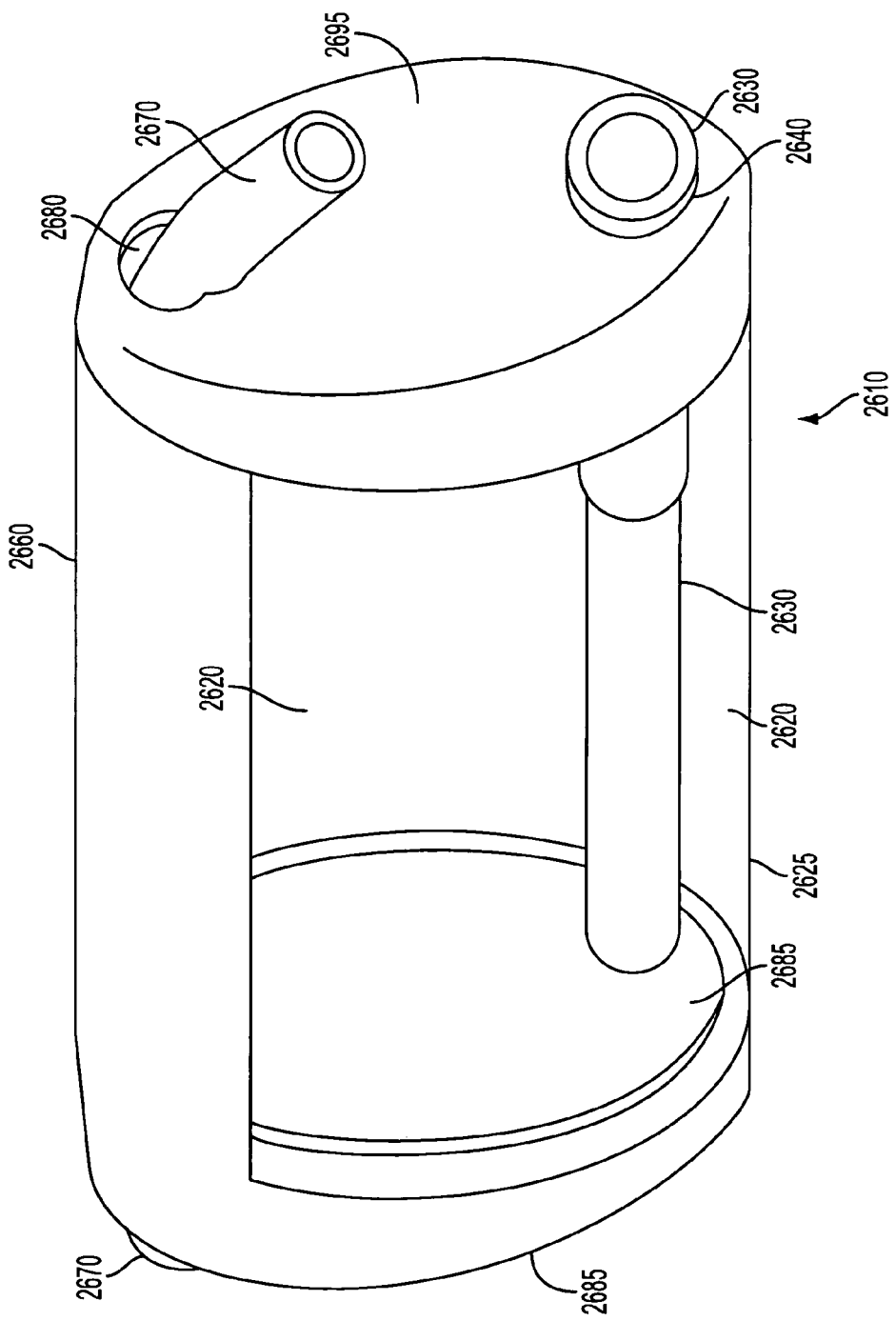
FIG. 28 shows a right-side perspective view of the mixing bottle apparatus according to the fifth embodiment of the invention.

FIGS. 26, 27 and 28 show different views of a mixing bottle 2610 according to a fifth embodiment of the invention. The mixing bottle 2610 is structured to couple to a small or medium-sized handpiece. As an example of a small handpiece, any of the ones shown in FIGS. 19, 24a–c, and 25a–d may be utilized. FIGS. 11 and 12 show a medium-sized handpiece, which may be 6–10 cm long by 2–4 cm wide, for example. The mixing bottle 2610 includes a first region 2620 that holds abrading crystals (crystals not shown in FIGS. 26, 27 and 28). A tube 2630 is provided in the first region 2620, whereby the tube 2630 provides a pathway for a crystal/air mixture to go from the first region 2620 to a handpiece (not shown in FIGS. 26, 27, and 28, but it is configured to be coupled to a top portion of the mixing bottle 2610 by way of tubes 2670 and 2630) and thereby to a patient's skin.

As shown in FIGS. 26, 27 and 28, the first region 2620 is a semi-oval region that is enclosed from an outer atmosphere by way a semi-oval part 2625, which is preferably a rigid plastic part. The semi-oval second region 2660, which is preferably a rigid plastic part, forms the rest of the oval, so that the combination of the semi-oval second region 2660 and the semi-oval part 2625 forms most of the oval mixing bottle 2610. The semi-oval part 2625 is preferably a see-through part, to allow an operator to determine the remaining amount of crystals within the mixing bottle 2610 during a dermabrasion treatment.

The mixing bottle 2610 also includes a cap 2695 and a base 2685, both preferably rigid plastic parts. As shown in FIGS. 26, 27 and 28, the base 2685 may be molded along with the part forming the second region 2660 as a unitary part, but it may alternatively be manufactured as a part separate from the part forming the second region 2660.

The base 2685 has an opening or port 2697 to allow a bottom portion of a tube 2670 to pass therethrough. The cap 2695 has a first opening or port 2640 to allow the tube 2630 to pass therethrough, and the cap 2695 has a second opening or port 2680 to allow a top portion of the tube 2670 to pass therethrough. The cap 2695 and the base 2685 are preferably rigid plastic parts.

In the preferred configuration, a vacuum provided by way of a vacuum source (see element 12 in FIG. 1, for example) that is situated downstream (with respect to the mixing bottle) of a collecting bottle (see element 17 in FIG. 1, for example), is used to suck air and crystals, as an air/crystal (or an air/reducing substances) mixture, into the tube 2630 and thereby into a handpiece (not shown in FIG. 26) that is coupled to a top end of the tube 2630. The top end of the tube 2630 extends slightly out (e.g., 1 to 3 cm) of a port 2640 of the mixing bottle 2610. An outer circumferential surface of the tube 2630 is snugly fit against an inner circumferential surface of the port 2640, to provide an air-tight fit. For example, the leg 2420 of the handpiece 2410 of FIG. 25a may be fitted within the top end of the tube 2630, whereby the tube 2630 is sized to allow the leg 2420 of the handpiece to be snugly fit therewithin, in an air-tight coupling.

Alternatively, one end of a small-sized flexible tubing may be fitted over the top end of the tube 2630 and the other end of the flexible tubing may be fitted over the "air/crystal entrance leg" 2420 of the handpiece 2410, to provide the air-tight coupling of those components. By way of example but not by way of limitation, the length of the flexible tubing may be 2 to 6 centimeters.

The crystals within the first region 2620 of the mixing bottle 2610 enter into the tube 2630 by way of a small opening (e.g., 1 to 5 millimeters) on a side surface of the tube (not shown, but see opening 26' in the tube 26 within the mixing bottle 15 shown in FIG. 4, for example, for a description of such an opening). In the preferred construction, there are no other openings in the tube 2630 that are provided within the first region 2620 of the mixing bottle 2610.

When a handpiece is coupled in an air-tight manner to the tube 2630 (disposed within the first region 2620) and to the tube 2670 (disposed within the second region 2660) disposed within the mixing bottle 2610, and when the opening of the handpiece (e.g., see opening 2440 of handpiece 2410 shown in FIG. 25a) is pressed against the skin of a patient, thereby effectively closing the opening to the external atmosphere, vacuum caused by a vacuum device that is disposed downstream of a collecting bottle results in air being sucked from the first region 2620 of the mixing bottle 2610, along with crystals being sucked from the first region 2620. The air and crystals are sucked into the opening of the tube 2630, and thereby provide an air/reducing substances mixture to a handpiece that is coupled to the mixing bottle 2620 (by way of its coupling to the top end of the tube 2630).

The mixing bottle 2610 also includes the second region 2660 that is sealed off from the first region 2620. The second region 2660 has the tube 2670 that is situated therein and which passes through an entire length thereof. A top end of the tube 2670 is preferably curved in order to couple to an angled leg of a handpiece. The top end of the tube 2670 extends slightly outside (e.g., 2 to 6 cm) of the second region 2660. The top end of the tube 2670 extends out of a port 2680 of the cap 2695, whereby there is no requirement that the disposition of the tube 2670 within the port 2680 of the cap 2695 be an air-tight fit.

For example, the "air-crystal-abraded tissue exit leg" 2430 of the handpiece 2410 shown in FIG. 25a is coupled to the angled first end of the tube 2670 in an air-tight manner, whereby in one configuration the leg 2430 is snugly fit within the top end of the tube 2670 to provide an air-tight coupling. Alternatively, one end of a small-sized flexible tubing may be fitted over an upper end of the tube 2670 and the other end of the flexible tubing may be fitted over the "exit" leg 2430 of the handpiece 2410, to provide the air-tight coupling of those components to each other. The length of the flexible tubing may be 2 to 6 centimeters, for example. As stated previously, the top end of the tube 2670 is angled (e.g., between 30 to 60 degrees) to accommodate an angled handpiece, such as any of the angled handpieces shown in FIGS. 24a–c and 25a–d. Preferably, the tubes 2630, 2670 are of rigid or semi-rigid plastic construction.

In a not-shown alternative configuration, the top end of the tube 2670 is angled and extends only slightly out from the port 2680 of the cap 2695 at the top of the second region 2660 of the mixing bottle 2610, in a manner similar to how the top end of the tube 2630 extends out from the port 2640 (as seen in FIGS. 26, 27 and 28). With such a construction, a differently-constructed small or medium-sized handpiece, such as one shown in either FIGS. 11 and 12, for example, may be coupled to the mixing bottle 2610. In this manner, a handpiece is removably coupled to the mixing bottle 2610 in an air-tight manner.

In the fifth embodiment, the second region 2660 of the mixing bottle 2610 serves as a conduit to a collecting bottle (not shown, but see FIG. 15, for example), and thereby allows for a smaller-sized area required for coupling a mixing bottle, a handpiece, and a collecting bottle to thereby provide a workable dermabrasion apparatus.

In further detail, a bottom end of the tube 2670 is air-tightedly coupled to an inlet port of a collecting bottle (see port 30 in FIG. 5). The bottom end of the tube 2670 is disposed beneath the opening 2697 of the base 2685 of the mixing bottle 2610. This coupling allows for an air-tight path all the way from the mixing bottle 2610 to a vacuum device that is coupled to the collecting bottle (see port 29 in FIG. 5 which provides for an air-tight coupling of a vacuum device to the collecting bottle).

Another feature of the mixing bottle 2610 shown in FIGS. 26, 27 and 28 is its oval shape. By way of example and not by way of limitation, the mixing bottle 2610 may be 6–8 centimeters long in a first one direction (maximum length of an ellipse defining a two-dimensional span of the oval shape) and 2–4 centimeters in a second direction (minimum length of an ellipse defining a two-dimensional span of the oval shape). The oval shape allows an operator to easily grasp the mixing bottle 2610, and thereby perform a dermabrasion treatment of a patient by way of a handpiece that is coupled to a top end of the mixing bottle 2610. Since the handpiece is preferably small in size (by way of example and not by way of limitation, 2.5 cm long by 2.5 cm wide), it is not very feasible for the operator to hold onto the handpiece to treat portions of a patient's skin, and so the oval shape of the mixing bottle 2610 provides a larger and convenient place for the operator to place his or her hand (e.g., thumb on one side of the oval shape, and one or more fingers on the other side of the oval shape) while treating a patient by way of the handpiece coupled to the mixing bottle 2610. That is, as the mixing bottle 2610 is moved in a particular direction by the operator, the handpiece (coupled to the mixing bottle 2610) moves in the same direction.

In a not-shown sixth embodiment, there is no enclosed second region; rather, the tube 2670 is situated outside of the oval-shaped mixing bottle. The tube 2670 is preferably tightly fitted onto the outer surface of the mixing bottle, such as by one or more rubber bands, clamps, or other types of removable adhering devices. The tube 2670 still extends out from the port 2680 of the mixing bottle 2610 (see FIG. 26), but again no enclosed second region would exist in this alternative configuration. This configuration according to the sixth embodiment may be slightly easier to manufacture as compared to the "enclosed" second region configuration of the fifth embodiment described previously. Preferably, for either the fifth or sixth embodiments, the mixing bottle is made from plastic or other vetrous material. The handpiece is preferably made from glass, due to the high speed crystals flowing therein, which would otherwise eat away a plastic part.

While preferred embodiments have been described herein, modification of the described embodiments may become apparent to those of ordinary skill in the art, following the teachings of the invention, without departing from the spirit and scope of the invention as set forth in the appended claims.

For example, after manufacturing of the disposable components making up the dermabrasion kit, such as the mixing bottle, the collecting bottle, the handle, and the pipes or tubes (preferably bendable plastic) that connect these elements together, they can then be placed in a bag, and then sealed. The components may be totally sterilized prior to placement in the bag. Alternatively, the components may be not sterilized or may only be partially sterilized prior to placement in the bag. The bag is preferably a sealable plastic bag (e.g., polyethelene). After the components have been placed in the bag, the bag is then subjected to gamma rays, in order to sterilize the components in the bag. That way, for the first case where the components are sterilized prior to placement in the bag, any contaminants introduced into the components during the placement of the components into the bag (and due to any impurities in the bag itself) would be removed, and, for the second case where the components were not sterilized or were only partially sterilized prior to placement in the bag, the complete sterilization of the components is performed while the components are in the sealed bag by the application of gamma rays to the bag. The second case allows for manufacturing of the components in a non-sterile or partially-sterile environment, which would typically save on costs involved in the manufacturing of the collecting bottle, the mixing bottle, and the handle. The use of gamma rays applied to components in a sealed bag also applies to the embodiment where several components are integrally connected to each other, such as the integral mixing bottle/handle structure shown in FIG. 16 together with a collecting bottle, or a single integral structure of a mixing bottle, a handle and a collecting bottle that does not require any pipes to connect these elements together (since they are already integrally formed as a single unit or mono-block).

Also, while the present invention has been described using a mixing bottle and a collecting bottle, other shapes besides a 'bottle shape' for mixing and collecting of an air/reducing substances mixture may be contemplated while remaining within the scope of the invention as described herein. For example, the components may be of rectangular shape or of a more complex (e.g., tetrahedron) shape.

What is claimed is:

1. An apparatus for use in dermabrasion, comprising:
    a mixing bottle that comprises:
        a first enclosed region for holding reducing substances to be applied to a patient during a dermabrasion treatment;
        a cap that includes a first port and a second port, the cap defining a top surface of the first enclosed region;
        a first tube that is configured to fit within the first port and into the first region, one end of the first tube extending out from the first port; and
        a base defining a bottom surface of the first enclosed region; and
    a handpiece that is coupled to the first and second ports so as to be moveable is a same manner and direction as the mixing bottle,
    wherein the mixing bottle and the handpiece are rigid plastic components,
    wherein the mixing bottle further comprises:
        a second enclosed region that is adjacent to the first enclosed region; and
        a second tube that is configured to fit within the second port of the cap and to extend through the second enclosed region,
        wherein the second tube extends through a third port disposed on the base, and
        wherein the second tube is adapted to be coupled to a collecting bottle during the dermabrasion treatment, and wherein the second tube is adapted to provide the reducing substances from the handpiece to the collecting bottle after the reducing substances have been applied to a skin region of the patient.

2. The apparatus according to claim 1, wherein the first tube has a substantially linearly shape from end-to-end, and wherein the second tube has a bend at one end where the cap is located, to thereby allow the handpiece to be coupled to the first tube and the second tube.

3. The apparatus according to claim 1, wherein the handpiece is V-shaped.

4. The apparatus according to claim 1, wherein the cap and the base are rigidly attached to the first enclosed region at top and bottom ends thereof.

5. A mixing bottle and handpiece for use in dermabrasion, comprising:
    the mixing bottle comprising:
        a top portion having at least a first opening and a second opening;
        a first enclosed region in which a mixing tube is provided therein, the mixing tube extending through the first opening;
        a second enclosed region in which a collecting tube is provided therein, the collecting tube extending through the second opening; and
        a bottom portion having at least a first opening in which the collecting tube extends therethrough,
    the handpiece comprising:
        a first end that is coupled to the mixing tube; and
        a second end that is coupled to the collecting tube,
    wherein the collecting tube is adapted to be coupled to a collecting bottle to provide an air-tight coupling between the handpiece and the collecting bottle, and
    wherein the mixing tube provides an air/reducing substances mixture from the first enclosed region of the mixing bottle to the handpiece, to be provided to a skin region of a patient by way of the handpiece.

6. The mixing bottle and handpiece according to claim 5, wherein the mixing bottle is an oval-shaped cylinder to allow an operator to grasp the mixing bottle to thereby move the handpiece when treating the patient.

7. The mixing bottle and handpiece according to claim 5, wherein the mixing tube includes a first end and a second end, the first end being positioned inside of the first enclosed region and the second end being positioned outside of the first enclosed region, and
    wherein the collecting tube includes a first end and a second end, the first and second ends of the collecting tube being positioned outside of the second enclosed region.

8. The mixing bottle and handpiece according to claim 5, wherein the mixing tube has a substantially linearly shape from end-to-end, and wherein the collecting tube has a bend at one end where the cap is located, to thereby allow the handpiece to be coupled to the mixing tube and the collecting tube.

9. The mixing bottle and handpiece according to claim 5, wherein both the mixing bottle and the handpiece are rigid plastic parts.

10. The mixing bottle and handpiece according to claim 5, wherein the handpiece is V-shaped.

11. A mixing bottle and handpiece for use in dermabrasion, the mixing bottle comprising:
   a top portion having at least a first opening and a second opening;
   an enclosed region in which a mixing tube is provided therein, the mixing tube extending through the first opening; and
   a bottom portion having at least a first opening in which a collecting tube extends therethrough;
the handpiece comprising:
   first and second ends respectively coupled to the mixing tube and the collecting tube,
   wherein the collecting tube is adapted to be coupled to a collecting bottle to provide an air-tight coupling between the handpiece and the collecting bottle, and
   wherein the mixing tube provides an air/reducing substances mixture from the enclosed region of the mixing bottle to the handpiece, to be provided to a skin region of a patient by way of the handpiece.

12. The mixing bottle and handpiece according to claim 11, wherein the mixing bottle is an oval-shaped cylinder to allow an operator to grasp the mixing bottle to thereby move the handpiece when treating the patient.

13. The mixing bottle and handpiece according to claim 11, wherein the mixing bottle and handpiece are rigid plastic parts.

14. The mixing bottle and handpiece according to claim 11, wherein the handpiece is V-shaped.

15. The mixing bottle and handpiece according to claim 11, wherein the collecting tube is adapted to provide the air/reducing substances mixture to a collecting bottle, after the air/reducing substances mixture has been applied to the skin region of the patient.

* * * * *